United States Patent [19]

Barrett, Sr.

[11] Patent Number: 5,460,188

[45] Date of Patent: Oct. 24, 1995

[54] METHOD OF INDUCING SAFETY IN SEXUAL ACTS AND AIDS IN SUPPORT THEREOF

[75] Inventor: Ronald A. Barrett, Sr., Chichester, N.H.

[73] Assignee: Academy of Applied Science; a part interest

[21] Appl. No.: 88,918

[22] Filed: Jul. 7, 1993

Related U.S. Application Data

[63] Continuation of Ser. No. 786,080, Oct. 31, 1991, abandoned.

[51] Int. Cl.$^6$ ........................................... A61F 6/02
[52] U.S. Cl. .......................... 128/842; 206/69; 128/844
[58] Field of Search ........................ 128/842, 844, 128/918; 604/347–353; 2/48, 247, 249, 250, 251; 206/69

[56] References Cited

U.S. PATENT DOCUMENTS

| | | | |
|---|---|---|---|
| 2,544,840 | 3/1951 | Kowatsch | 2/252 |
| 3,065,471 | 11/1962 | Lea | 2/113 |
| 3,137,866 | 6/1964 | Stephens | 2/248 |
| 3,537,108 | 11/1970 | Daniels | 2/252 |
| 3,611,444 | 10/1971 | Rector | 2/247 |
| 3,624,686 | 11/1971 | Beals | 2/48 |
| 3,840,901 | 10/1974 | Eyster | 2/247 |
| 3,871,030 | 3/1975 | Green | 2/250 |
| 4,266,300 | 5/1981 | Partridge | 2/247 |
| 4,388,734 | 6/1983 | Cowden | 2/250 |
| 4,446,573 | 5/1984 | Green | 2/247 |
| 4,852,188 | 8/1989 | Marsh | 2/250 |
| 4,899,395 | 2/1990 | Spector | 2/250 |
| 4,989,273 | 2/1991 | Cromartie | 2/250 |
| 5,044,492 | 9/1991 | Auerbach | 206/69 |
| 5,067,178 | 11/1991 | Katchka | 2/250 |
| 5,172,430 | 12/1992 | Lerma-Solis | 128/844 |

*Primary Examiner*—Michael A. Brown
*Attorney, Agent, or Firm*—Rines & Rines

[57] ABSTRACT

A method and garment aid to facilitate and induce the use of a condom for safe or safer sexual acts are disclosed, wherein a pocket containing a condom is carried, for example, at the inner forward waistband region of underpants, such that a potential participant, when removing such underpants, as a general precondition to engaging in the sexual act, will invariably touch or be conscious of the pocket-and-condom, thus providing a warning and a reminder of the proximal presence and readily accessible convenience of the juxtaposed condom that may serve to induce use of the same and thereby increase the chances of the enactment of safe or safer sex. Novel pockets including modified condom-package-pockets are disclosed.

4 Claims, 1 Drawing Sheet

METHOD OF INDUCING SAFETY IN SEXUAL ACTS AND AIDS IN SUPPORT THEREOF

This is a file wrapper continuation of parent application, Ser. No. 786,080, filed Oct. 31,1991, now abandoned.

The present invention relates to the problem of inducing participants in sexual acts to seek safety from disease and unwanted pregnancies through the use of condoms; being more particularly directed to methods of and aids in support of providing ready inducement, warning and convenience as inherent pr-conditions of the sexual act are performed.

BACKGROUND OF INVENTION

Worldwide educational programs are in sway, particularly in the light of the terrible and deadly affliction of AIDS and the seriousness of venereal and other diseases and unwanted pregnancies, to urge the use of condoms as at least a substantial measure for providing relative safety.

Unfortunately, in the heat of human passion, often uncontrolled, particularly with younger people, the participants are frequently unprepared, or find it inconvenient, or lack the will power, or suffer memory lapses as to the seriousness of their risks, and do not use condoms.

It is to the automatic or inherent solution or at least amelioration of these circumstances that lead to ignoring the use of condoms, that the present invention is primarily directed.

OBJECTS OF INVENTION

The object of the present invention, indeed, is to provide a novel method of facilitating a safe sexual act and aids in support thereof, by providing for the ready and most easily accessible presence of a condom to the participant, as underpants or similar garments are removed by the participant as a usual pre-condition to the act, and during which the participants cannot help but touch and/or see the warning and have the condom at their fingertips in the very undressing movements they perform.

Other and further objects will be explained hereinafter and are more fully delineated in the appended claims.

SUMMARY

In summary, the invention embraces a method of facilitating a safe sexual act, that comprises, storing a condom on the underpants of a potential participant, readily to facilitate and induce its use by inherently reminding the participant of its presence and convenience and serving as a warning for safety as the underpants are being removed as a pre-condition of the act; said storing being effected by a pocket housing the condom at the forward waist region of the underpants and of minimal thickness, bulk and contour about the condom to render its presence substantially imperceptible in the feel and sound in the wearing of the underpants, said pocket sealing the condom from inadvertent removal therefrom, including during the washing of the underpants, while enabling the ready unsealing to permit facile withdrawal and use of the condom.

As an aid to practicing this method, the invention also includes modified underpants for facilitating a safe sexual act, having in combination with elasticized waistband underpants, a pocket attached to a predetermined region, preferably forward waistband region, of the underpants and adapted to house and store a condom, readily to facilitate and induce its use by inherently reminding the potential participant of its presence and convenience and serving as a warning for safety as the underpants are being removed as a pre-condition of the act; the pocket being provided with a readily openable edge or region for exposing the condom and being of minimal thickness, bulk and contour about the condom to render its presence substantially imperceptible in the feel and sound in the wearing of the underpants; said pocket, when closed, storing the condom from inadvertent removal therefrom including during washing of the underpants, but with said edge or region readily openable to permit facile withdrawal and use of the condom.

Preferred and best mode embodiments and pocket designs are hereinafter detailed, including:

(1) an underpants pocket, preferably of fabric similar in feel and appearance to that of the underpants, permanently or detachably secured at or near preferably the forward portion of the elasticized waistband of the underpants, and normally closed, but readily openable along a predetermined edge or region to permit access to and withdrawal of the condom; and (2) a pocket serving as the condom package itself, with an external adhesive or adhering surface or coated edge or region, normally covered by a release strip, that attaches to and is removable from the underpants or similar surface.

DRAWINGS

The invention will now be described with reference to the accompanying drawings, FIG. 1 of which is an isometric view of the pocket invention herein incorporated in a pair of underpants;

DESCRIPTION OF PREFERRED EMBODIMENTS

Figure 1:
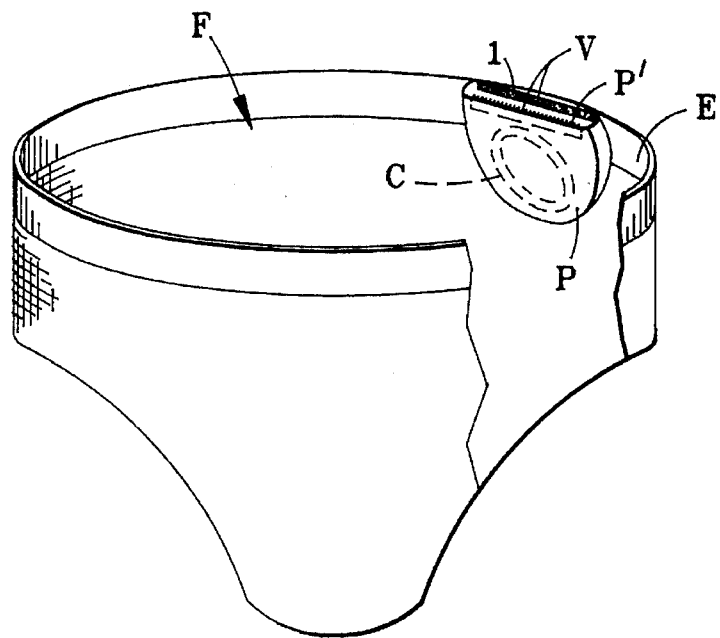

Referring to FIG. 1, a pocket P containing or housing a condom C is shown integrated or attached with and hanging from, preferably, the inside elastic waistband region E of the forward or front portion of fabric underpants F. As shown, the pocket is a fabric similar to that of the underpants and of minimal thickness, bulk and contour about the condom, generally conforming thereto, to render the presence of the pocket substantially imperceptible in feel and sound in the wearing of the underpants. The attachment of the pocket P to or near the waistband E in the embodiment of FIG. 1 is shown permanent, as by stitching to the waistband at 1 with the pocket freely hanging or suspended therebelow. The upper or top pocket edge P' (though other regions may be selected) is shown provided with hook-and-loop strips V on opposing inner margins to close off the pocket and seal the condom from inadvertent removal therefrom, including during the washing of the underpants, while enabling the ready opening of the edge to permit facile withdrawal and use of the condom (and subsequent replacement of another condom(s)).

Through the above type of construction and particular placement, one who is to participate in a sexual act will customarily, as a pre-condition thereto, place their fingers on the upper elasticized waistband region of the underpants to stretch the waistband to remove the underpants, inherently intercepting the pocket and receiving the warning and being reminded of the proximal presence and readily accessible convenience of the juxtaposed condom, and thus likely inducing the use of the same, increasing the chances of the enactment of safe or safer sex.

Figure 2:
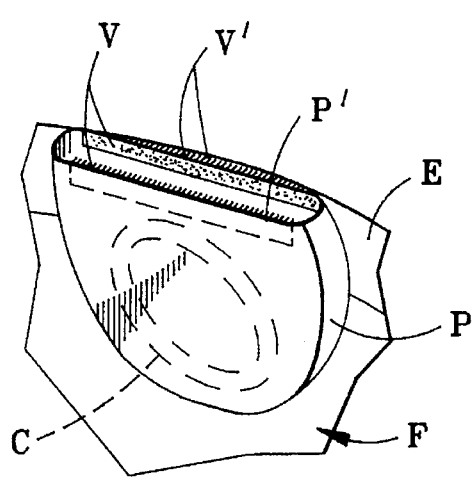
FIG. 2 is an enlarged view of a detachable version of the pocket of FIG. 1.

Instead of a permanent integrated pocket attachment, as at 1 in FIG. 1, opposing hook-and-loop strips V' on the elastic waistband region and the juxtaposed outer top marginal surface of the pocket P may be provided, as shown in FIG. 2, enabling ready attachment and removal of the hanging pocket from the undergarment, where desired.

While the use of a fabric or material pocket similar to that of the underpants has been previously described as a desirable mode, where such overall integration with the garment is not particularly desired, the pocket material may be different.

Figure 3:
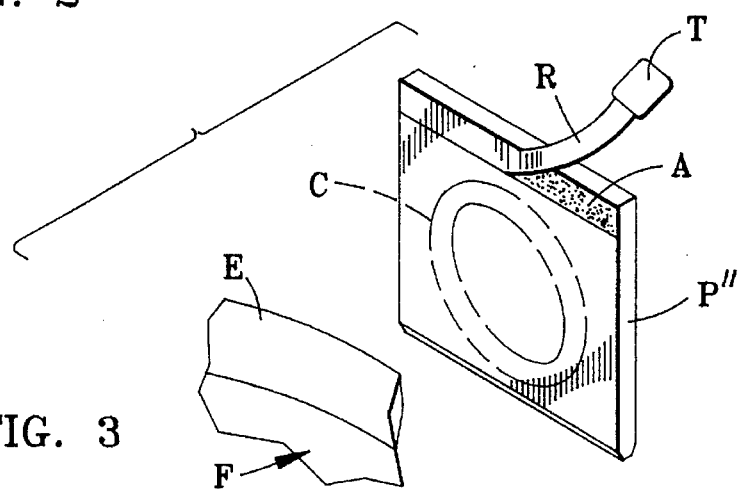
FIG. 3 is a further modification wherein the condom package itself, modified to enable attachment and removal from the underpants, serves as the pocket.

Indeed, the current day plastic or metallized packages housing and generally conforming to condoms sealed therein, and tearable to open the same at a desired edge or other region for the withdrawal of the contents, may, with modification, become enabled to serve as the pocket of the invention, as shown, for example, at P" in FIG. 3. In such event, an outside surface region of the condom package (pocket) P" may be provided with an adhesive coating or other adherent surface, such as any well-known pressure-release adhesive A, along, for example, an upper margin of the outside surface of the package. Normally, the strip A would be covered by a release strip R, as of silicone, preferably having a tab T that extends slightly to the side of the package or other means to enable easy removal of the release strip. When the release strip R is torn off, the exposed adhesive strip A will enable ready attachment to the waistband E or other part of the underpants (or other garment or surface, as desired), with the feature of ready removal and opening of the carried condom-package-pocket prior to the sexual act.

Further modifications will also occur to those skilled in this art, including integration of pockets in non-fabric undergarments, and in providing the pockets in other garments, as well, or on other surfaces, particularly those that are inherently intercepted as the participants prepare for a sexual act, and other than hook-and-loop type attaching strips may also be used; such being considred to fall within the spirit and scope of the invention as defined in the appended claims.

What is claimed is:

1. A permanently sealed metallized or plastic condom package adapted to be attached to clothing such as an elasticized waistband undergarment or other surface and containing a condom sealed therewithin, said metallized or plastic package being provided with a pressure-release-adhesive coated on the outside surface of the metallized or plastic package itself along an external region thereof to enable ready attachment to and removal from such clothing, said adhesive coating being normally covered with a release strip removable to expose the adhesive and permit attachment to the clothing along the adhesive coating, and said metallized or plastic package being detachable from the clothing by pulling the package along the adhesive attachment and being tearable to break the seal and enable its opening for withdrawal of the condom.

2. A metallized or plastic condom package as claimed in claim 1 and in which said external region of the metallized or plastic package is located along an edge.

3. A metallized or plastic condom package as claimed in claim 2, and in which said edge is an upper or lower edge at which the condom package is attached to the clothing, otherwise to hang freely therefrom.

4. A permanently sealed metallized or plastic condom package temporary pocket to be attached to clothing such as an elasticized waistband undergarment or other surface and for storing a condom sealed therewithin, said metallized or plastic pocket being provided on the outside surface of the metallized or plastic package itself with a hook-and-loop type strip to enable ready hanging attachment and removal from a cooperative hook-and-loop type strip carried by the said clothing or other surface, and said metallized or plastic pocket being tearable to break the seal for withdrawal of the condom.

\* \* \* \* \*